United States Patent [19]
Abrahams et al.

[11] 3,981,620
[45] Sept. 21, 1976

[54] PUMPING APPARATUS

[75] Inventors: Louis Abrahams, Worcester; Burleigh M. Hutchins, Jr.; James L. Waters, both of Framingham, all of Mass.

[73] Assignee: Waters Associates, Inc., Framingham, Mass.

[22] Filed: Nov. 19, 1973

[21] Appl. No.: 417,146

Related U.S. Application Data

[62] Division of Ser. No. 232,128, March 6, 1972, Pat. No. 3,855,129.

[52] U.S. Cl. ............................ 417/42; 417/539; 417/568
[51] Int. Cl.² ............................ F04B 49/00
[58] Field of Search ............ 417/42, 13, 43, 44, 417/45, 24, 454, 343, 901, 12, 568, 326; 92/86.5, 129, 130, 168

[56] References Cited
UNITED STATES PATENTS

| | | | |
|---|---|---|---|
| 479,960 | 8/1862 | Van Depoele | 417/326 |
| 2,010,377 | 8/1935 | Sasson | 417/539 |
| 2,535,617 | 12/1950 | Westbrook | 417/24 |
| 3,016,843 | 1/1962 | Smith | 417/471 |
| 3,125,963 | 3/1964 | Whitley et al. | 92/168 |
| 3,145,629 | 8/1964 | Gottzmann | 417/901 |
| 3,298,319 | 1/1967 | Savage | 417/568 |
| 3,301,189 | 1/1967 | Kling | 92/129 |
| 3,330,217 | 7/1967 | Bauer et al. | 417/454 |
| 3,670,630 | 6/1972 | Tyson et al. | 92/129 |
| 3,737,251 | 6/1973 | Berman et al. | 417/12 |
| 3,749,525 | 7/1973 | Hooper | 417/343 |
| 3,810,716 | 5/1974 | Abrahams et al. | 417/313 |
| 3,816,029 | 6/1974 | Bowen | 417/539 |

*Primary Examiner*—William L. Freeh
*Attorney, Agent, or Firm*—Cesari and McKenna

[57] ABSTRACT

A compact pumping system especially useful in liquid chromatography wherein comprising a liquid path which is fully flushed in each stroke of a pump, a pump which provides substantially pulse-free flow, a pressure-sensor integrated into said flow path and operably connected to the control circuit of a bifilar stepping motor. This circuit is so designed that the driving current applied to the motor is only that required to pump the liquid. The avoiding of heat associated with a greater current is particularly important in forming a compact package of motor and pump for use in liquid chromatography.

15 Claims, 12 Drawing Figures

PUMPING APPARATUS

This is a division of application Ser. No. 232,128, filed Mar. 6, 1972, now U.S. Pat. No. 3,855,129.

BACKGROUND OF THE INVENTION

This invention is primarily directed towards improvements in a liquid feed apparatus for use in liquid chromatography systems. However, the pumping unit and various aspects thereof are useful wherever a precise, controlled movement of liquid is desired and, notably, in the movement of physiological liquids in the medical field and movement of fluids in analytical processes other than chromatography. Moreover, the various aspects of the invention include specific improvements in the field of controlling a pump drive means, measuring liquid pressure, and pump design.

Because the invention was made with the immediate aim of solving problems relating to liquid delivery systems used in liquid chromatography systems, the background relevant to such problems is set forth hereinbelow:

Liquid chromatography is a system whereby a mobile liquid phase is passed through a compartment containing a stationary phase. During the passage of the liquid phase, it interacts physically or chemically with the stationary phase. This interaction results in a separation of components in the liquid phase. Such a separation is usually manifested by the fact that different components in the liquid phase pass through the stationary phase at different rates. An analysis of samples of the effluent from the compartment taken over a period of time provides a basis for determing the chemical composition of the input liquid.

The analysis of the efflux is usually made continuously with a refractometer or the like.

It is desirable to supply the liquid to the aforesaid chromatography compartment (usually an elongate column packed with particles) at very high pressures, usually from 100 to 10,000 psig.

A number of other attributes are desirable for pumping systems used in chromatography:

They should have a wide operating range in terms of pump throughput capcity.

They should have a minimal temperature deviation from the temperature of the fluid being processed. Thus a motor integral with the pumping system should be either very well insulated from the liquid being pumped or should run at a temperature close to the temperature of the liquid.

There should be a minimum flush time in which one liquid being pumped can be replaced by another liquid being pumped.

The pumping system should be capable of providing means to moderate the pump output capacity in response to pump output pressure, and this moderating means should be sensitive enough to allow compensation for compressibility on the pump output side of the system, whether this compressibility be a characteristic of fluid being pumped or of the pumping system itself.

The pumping system should include protective means to shut down the pump in an emergency, i.e. when the outlet pressure reaches a certain level.

The pump should provide as little mixing of the liquid being pumped as is possible and preferably so little mixing that recycling of the liquid through the pump is feasible.

The pumping action should be steady, i.e. pulseless.

In general the above-listed attributes tended to be selfconflicting when a chromatography system was operated according to the methods of the prior art. For example, the use of pulse dampeners tended to result in undersirable mixing of the fluid. Yet pulse-imparting pumps were those most acceptable for reaching the desired high feed pressures. And motors used to drive said pumps generated considerable heat — enough to affect the characteristics of the fluids being pumped when the motor was packaged proximate the pump as is convenient and customary. Moreover, conventional pressure sensing means required dead space in which liquid would become relatively stagnant and from which it could not be quickly flushed when one wished to change the liquid being pumped.

Applicants therefore set as their objectives to provide liquid delivery apparatus and processes having a number of the above-listed attributes and overcoming many of those problems relating to conflicting design requirements.

SUMMARY OF THE INVENTION

In the pumping system of the invention, the primary advances in the art have been made under the general categories of 1) pump motor and control means, 2) construction of the pump itself, 3) pressure-sensing means, and the various combinations of these advances. It will be manifest, to those skilled in the art on reading the instant application, that some of the advantages obtainable by using all the features of the invention will be attainable by constructing apparatus using only some of the features of the invention.

Pump Construction

The pump of the invention is provided with a plurality of plungers operated with drive linkage between the motor and the plungers which cause the output of the pump to be substantially constant with time. Although any operable drive linkage may be used to achieve this purpose, a particularly advantageous linkage comprises the use of a drive gear between a) the pump motor and b) a plurality of eccentric gears connected to the plunger of the pump so that the plungers will be dependably operated in proper cycle relationship to obtain the desired constant output of the pump.

Other advantageous features of the pump include a) novel check valve means, which assure the timely and leak-proof closure of the inlet and outlets to the pump chambers, b) novel drive linkage between each plunger and its drive shaft whereby the plunger is allowed to seek its own center line, and wearing of the pump chamber seal means by the plunger is fully avoided, c) a feature whereby the plunger is machined to have a diameter which is sufficiently smaller than the chamber in which it reciprocates so that, on the plunger's movement through the chamber, fluid being displaced from the chamber follows a flow path generally defined by the annular space between the advancing plunger and chamber wall. This last feature allows the pump chamber to have what has been found to be highly important feature: a chamber that has its inlet at one end thereof, its outlet at the other end thereof and, consequently, a full-chamber flushing action at each stroke of the pump.

Pressure sensing means

If the pump motor and control means is to be responsive to the pressure of the liquid being pumped, it is necessary to provide a sensor for this pressure. It has been found most advantageous, in order to conserve the advantages inherent in the flow characteristics imparted to the liquid by the pump, to avoid use of conventional sensing means which require some dead liquid volume in which to place a sensor or which require some dead liquid volume to form a hydraulic contact with the sensor. A "flow-through" meter has been developed which comprises a conduit as its pressure-sensitive element. This conduit forms an integral, serially aligned, flow path of the liquid between the pump and the outlet of the liquid delivery system. In general, this device comprises, as its fluid-conducting element, a Bourdon tube and a displacement sensor which senses both the degree of movement of the tube and is operably attached to the motor control system.

After construction of the apparatus generally described above, it was found that a surprisingly large number of advantages were derived from its use in chromatographic applications. For example, solvent changes which took up to an hour in apparatus of the prior art could be achieved within 5 to 10 minutes with the apparatus of the invention.

So little peak-spreading, or mixing, was achieved with the system that it became entirely practical to recycle material to be analyzed through the pump again and still achieve so little mixing during recycle that analysis was not unduly hindered. Moreover, thermally sensitive liquids, i.e. liquids which have any undesirable physical or chemical reponse to heat can be processed most favorably with the system. For example, troublesome gas bubbles in the liquid can be avoided even on the suction stroke, because they are not promoted by excessive heat.

The chemical analysis, e.g. those made by a refractometer which is fed from a column supplied by the liquid feed system of the invention, show a better base line, and more accuracy in general because of the lack of pulses and thermally induced drift.

In summary, therefore, applicants have constructed a novel pump which can provide a constant flow over a period of hours, a generally pulseless flow, and an even flow. They have coupled with this pump, in a novel liquid delivery system, a novel pressure-sensing device which requires no liquid dead space and which serves to form part of a motor control circuit wherein it functions as both a safety, i.e. shut-down device and as a motor-speed governing means. Finally, applicants have incorporated a motor having a novel control circuit into their liquid delivery system, thereby providing not only a means to control the speed of the motor but a means to limit the current to said motor to that current actually required to drive the pump.

By so limiting the current, the amount of heat dissipated in the drive means or its control circuit is markedly reduced. This is extremely important when the motor and pump are both mounted on a common base or in a common housing or so close to one another that there would be a significant flow of heat from the motor to the pump were the pump maintained close to ambient and the motor reached an elevated temperature, e.g. 140°F or higher. In liquid chromatography, if motor-generated heat reaches the liquid being pumped, there is a problem of interfering bubbles being formed by gases forced out of solution. The problem can be especially severe on the suction stroke of a piston pump. The formation of such bubbles can unduly affect the compressibility of the liquid.

The quick-flushing characteristic of the pump and liquid delivery system of the invention is particularly efficient when no part of the liquid flow path through the pump or the system is more than 0.2 inches from the mean center line of the flow path of the liquid. By "flow path" in this connotation is meant the volume which is filled with liquid from the time it enters any given pump chamber to the time it leaves a downstream pressure sensor if one be used.

When "flushing" is referred to in this application it is defined as an action whereby fresh liquid displaces existing liquid in a segment of a flow path. Thus, if a conduit is 4 inches long, the entire conduit need not be flushed by each stroke as long as the liquid advances through the conduit, segment by segment, without by-passing any substantial dead space. By substantial dead space is meant that such as would be formed by dampening devices pressure sensors known to the prior art and other such devices which comprise compartments for receiving the liquid being pumped which compartments aare not in any sense flushed on each stroke of the pump.

In the most favorable embodiment of the invention for use in lqiuid chromatography, the total liquid volume within the liquid delivery system from pump inlet to pressure-sensor outlet will be less than 3 milliliters. It is advantageously lower, ie, less than 1.5 milliliters as is the case in the specific system described below.

ILLUSTRATIVE EXAMPLE OF THE INVENTION

In this application and accompanying drawings there is shown and described a preferred embodiment of the invention and suggest various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

Figure 1:
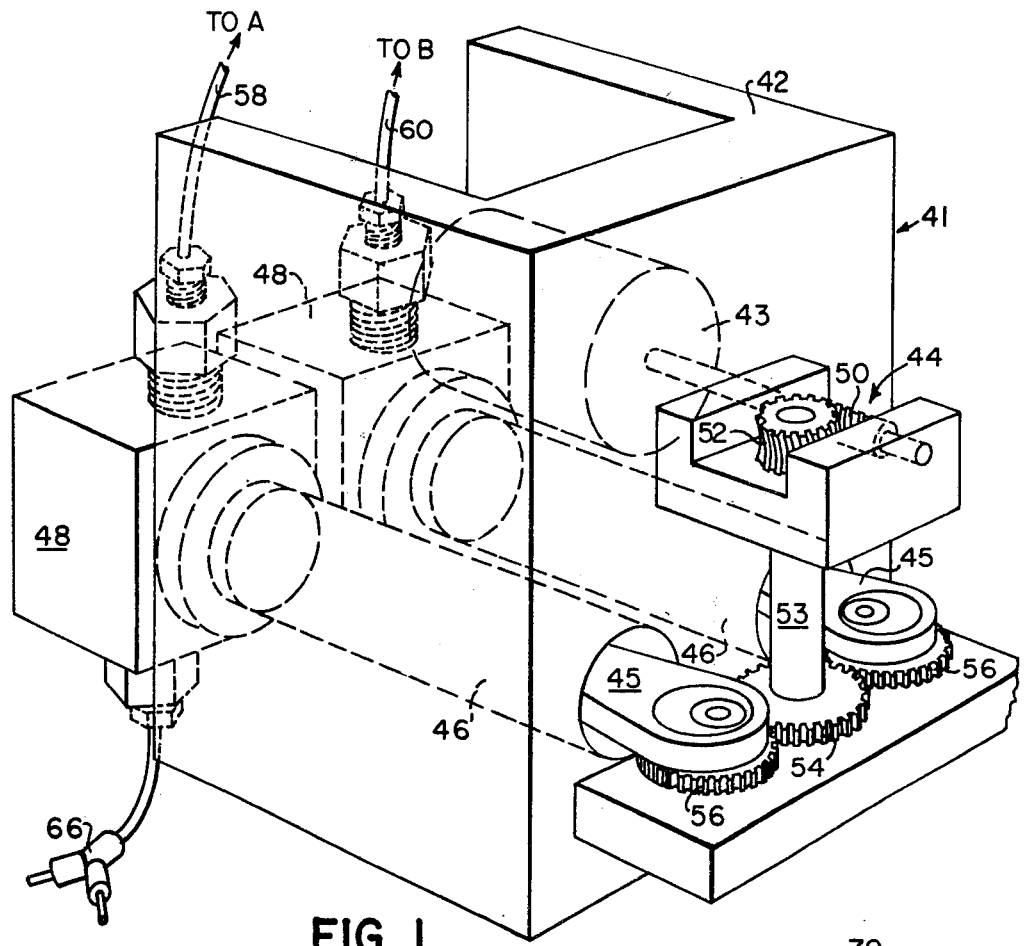
FIG. 1 is a perspective view indicating an arrangement of various parts of a pump constructed according to the invention.
Figure 4:
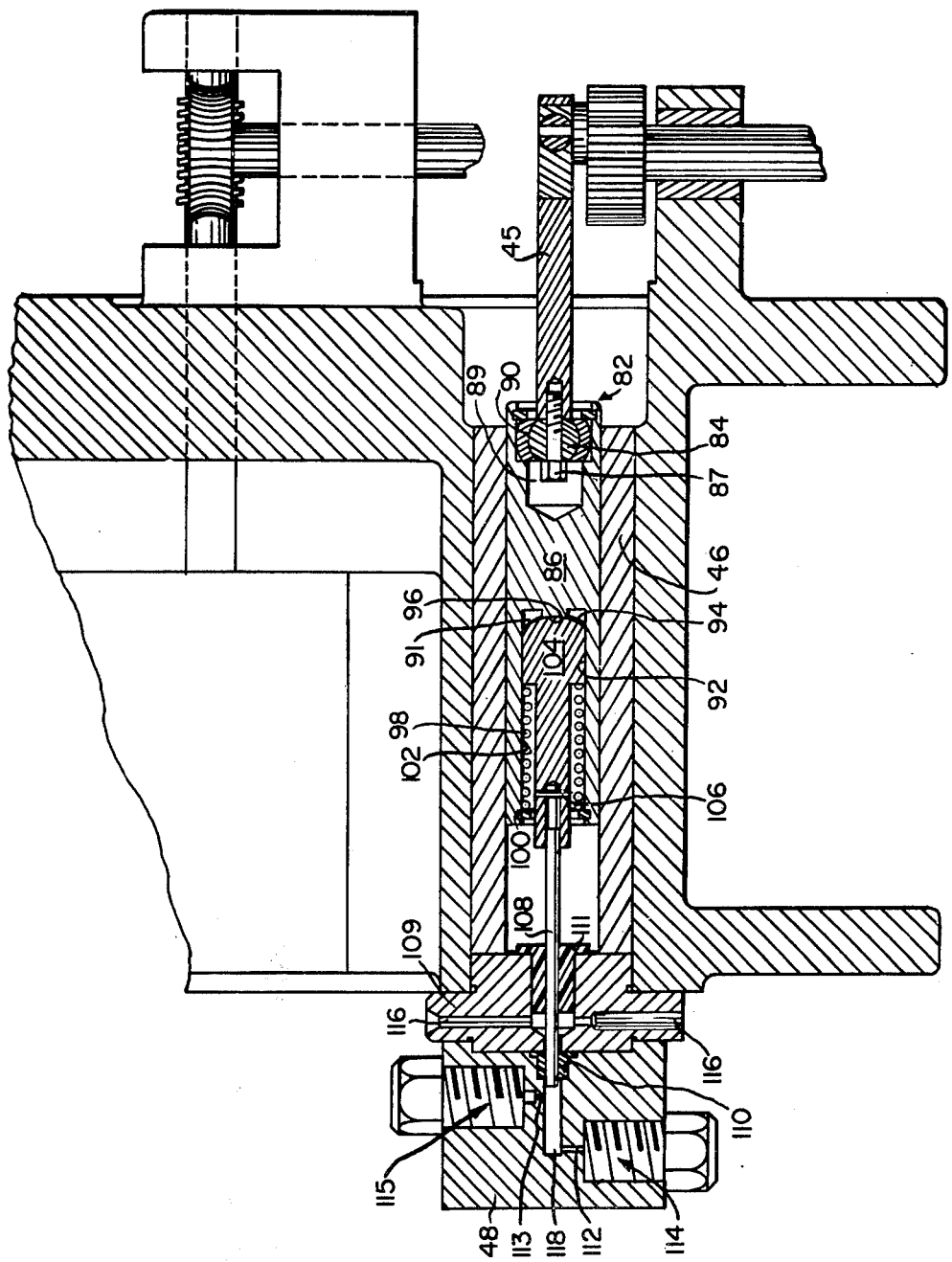
FIG. 4 is a fragmentary view of a portion of a pump constructed according to the invention showing the elements between the drive linkage and reciprocating plunger and numerous other parts in section.
Figure 5:
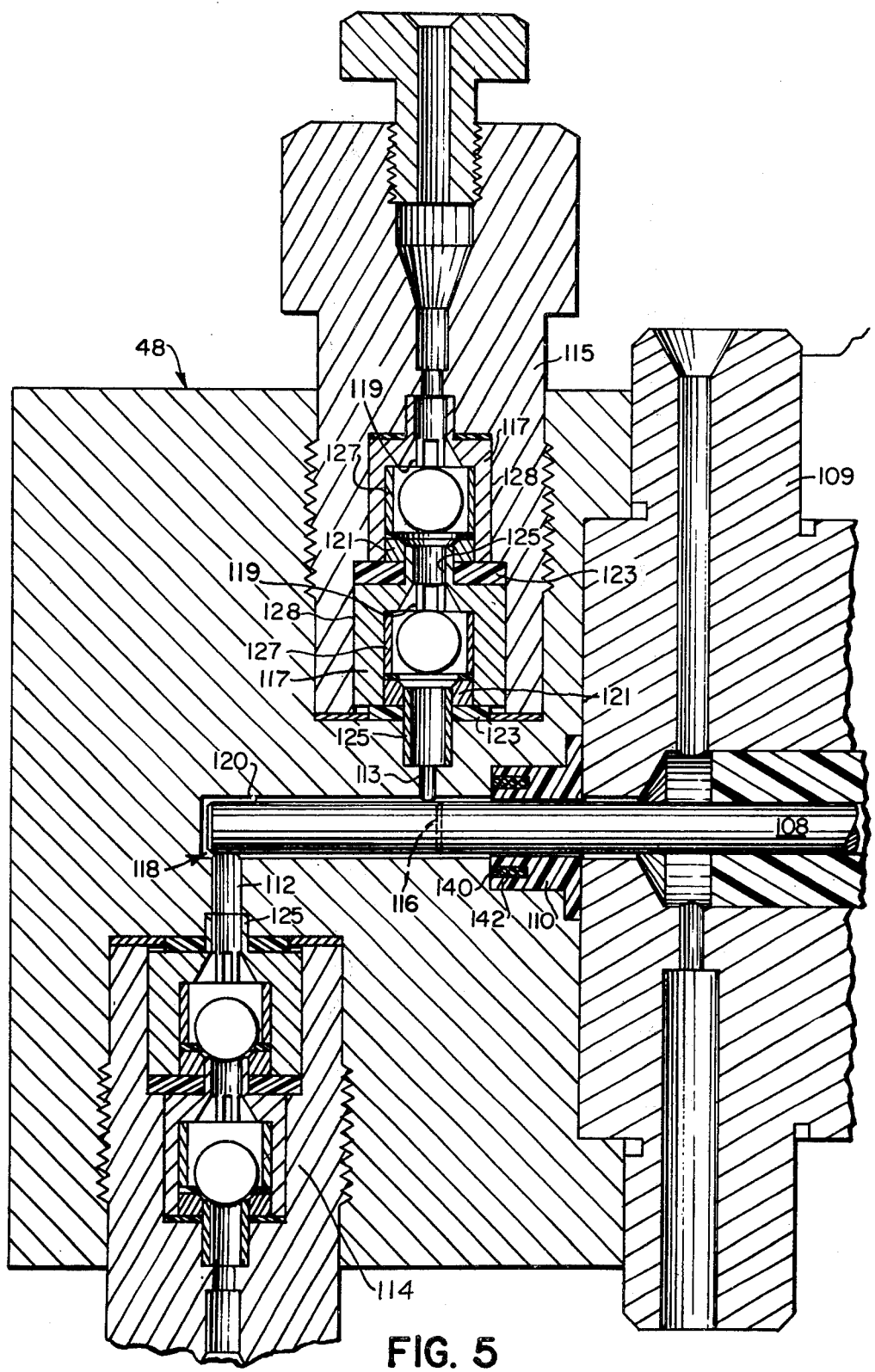
FIG. 5 is a detailed view of a pump chamber and inlet and outlet ports therefrom which have been constructed according to the invention.

Referring to FIG. 1, it is seen that a pumping unit 41 comprises a frame 42, a stepping motor 43 mounted thereon, a gear train 44 mounted to drive two crank arms 45 in two elongate cylindrical housings 46 each of which house plunger driving means, better seen in FIG. 4. Mounted at one end of housing 46 are pump heads 48, the details of which are also shown in FIGS. 4 and 5.

In general, stepping motor 43 drives worm gear 50, thence rotary gear 52 turns shaft 53 and a master elliptical gear 54. Gear 54 causes two eccentric gears 56, also elliptical in shape to operate crank arms 45 180° out of phase with one another so that the sum of the instantaneous displacement per unit time of all of the pistons in the pressurizing direction is a constant. This gear system is shown in more detail in FIG. 6.

Figure 3:
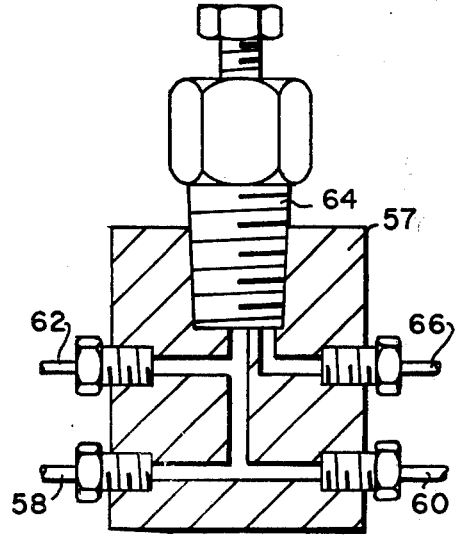
FIG. 3 is an outlet manifold used in conjunction with the pump such as is shown in FIG. 1.

FIG. 3 shows a manifold 57 which has inlet conduits from pump heads 48. It is within this manifold 57 that streams from the various pumpheads 48 are integrated into a single effluent stream. This effluent will normally exit from the manifold through conduit 62, but a valve 64 forms means to divert the flow through conduit 66 to flush the reference liquid of a differential liquid chromatographic detector.

Figure 2:
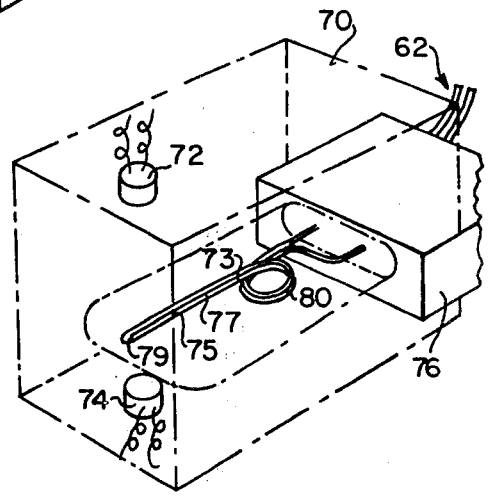
FIG. 2 is a perspective view of a novel pressure sensor elements useful in constructing the liquid delivery system of the invention. The housing is omitted to better illustrate the relative position of the various parts.

FIG. 2 illustrates a particularly advantageous pressure-sensing device utilized in the invention. It comprises a housing 70, a light source 72, a light sensor 74, and a Bourdon-tube 73 which forms an extension of conduit 62. In operation, the position of the straight portion 75 of Bourdon tube 73 is caused to change dependent on the pressure of liquid within the tube. This change in position of portion 75 of tube 73 results in a different amount of light from source 72 reaching sensor 74. The sensor normally a photoresistor, provides a direct means for sensing and signalling the pressure within tube 73. The signal so generated is applied to controlling the circuit of motor 43 and this mode of control will be described elsewhere in the specification.

Tube 73 is mounted to housing 70 by means of a stainless steel block 76 of about one-half inch in thickness. The tube is one-sixteenth inch in diameter and is comprised of two generally parallel segments 77 meeting at the midpoint 79 of straight portion 75 which extends beyond the helical segment 80 of the tube. Tube 73 is conveniently 0.005 to 0.10 inches in diameter.

Referring now to FIG. 4, it is seen that each cylindrical housing 46 comprises mechanical plunger driving means 82. This driving means is actuated by the movement of a crank arm 45 already described. Crank arm 45 is connected through a spherical bearing 84 positioned in a recess 89 of a piston 86. Bearing 84 is connected to crank arm 45 by fastening means 87.

Piston 86 which has been seen to comprise a recess 89 at one end thereof comprises at the other end thereof a recess 91 for receiving a plunger holder 92. Plunger holder 92 comprises a rounded spheroid surface 94 which normally abuts against the center of a flat bearing surface 96 on plunger 86. Holder 92 is further positioned by a spring 98 retained by a circlip 100 snapped into an annular recess on the interior wall 102 of recess 91. Spring 98 is a biasing means which pulls the plunger assembly back during its return stroke while biased against piston 86. It will be noticed however, that piston holder 92 is neither rotationally restrained nor is it restrained against axial movement relative to piston 86 when stresses on the piston require such movement. There is a sufficient difference in the outer diameter of positioning head 104 carrying surface 94 and the interior wall 102 of recess 91 to permit some positional adjustment of piston holder 92.

Attached to plunger holder 92 by a single pin 106 is plunger 108. Plunger 108 extends through a plunger support 109 and a seal means 110, both best shown in FIG. 5, into pump head 48. There is a cylindrical seal, 111, formed of a halocarbon resin which supports the plunger within support 109. The pump head is fitted with an inlet port 112, an outlet port 113 and check valve means 114 and 115 mounted in said port. Self-lubricating seal means 110 is mounted within head 48 and is held therein by plunger support 109. Ports 116 are provided in plunger holder 109 in case drainage is required because of seal 110 failure.

FIG. 5 illustrates in more detail, the pumping heads 48 and parts of the system directly associated with the heads. Seal 110 is constructed of a fiber-reinforced poly(tetrafluoroethylene) as such it has strength and a self-lubricating characteristic which helps to further minimize binding and wear between seal and plunger.

Plunger 108 is noted to have a forward path that just passes inlet port 112 and a backward motion, the rearwardmost position of which is defined by dotted line 116 just in back of outlet port 113. In the illustrative example, the plunger is about one-eighth of an inch in diameter and the pump chamber 118 in which it reciprocates is about 0.006 inches larger in diameter, thus forming an annulus 120 through which liquid sucked into chamber 118 during its backward stroke of the plunger can flow backwardly toward outlet 113 during the forward stroke of the plunger.

A proper register of the mechanical driving means 82 and the chamber 118 is assured by the use of plunger support means. 109 as a precision positioning coupling between the driving means 82 and the pump head 48.

FIG. 5 also discloses a novel check valve construction which can be illustrated with reference to outlet valve 115. Valve 115 comprises two, serially-arranged, flow checking assemblies 117 each comprising a ball element 119, a ball-seat 121, a gasket support tube 125. The support tube forms an integral part of the flow path and prevents the inward radial distortion of gasket 123. In case of the outwardmost support tube 125, it is integral with the housing 128 of the check valve. A sleeve 127 formed out of a self-lubricating resin is placed between the valve seat element and the housing element. Valve 114 is similar to, and shown in somewhat more detail than, Valve 115.

Note an annular slot 142 in seal 110 holds a spring forming means to assist in biasing the seal means in sealing relationship against the plunger.

Figure 6:
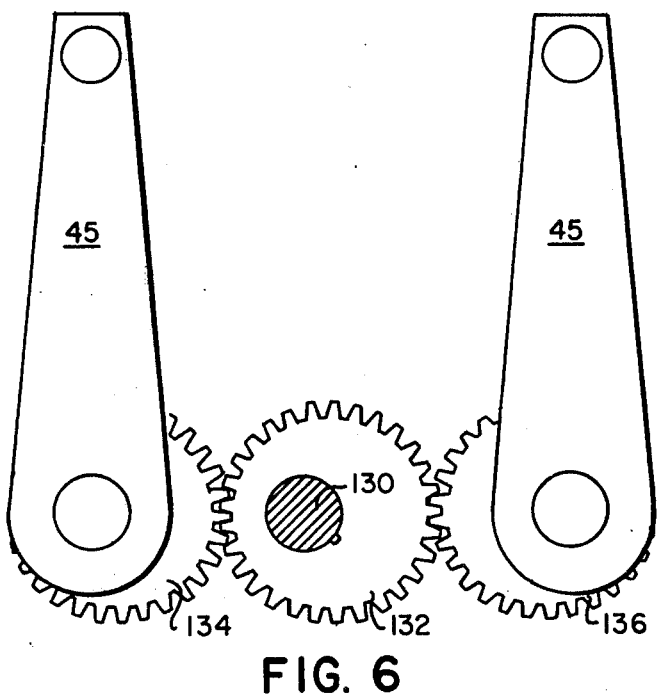
FIG. 6 shows a portion of a mechanical linkage between the motor drive of the pump and the pump plunger.

FIG. 6 shos an elliptical gear system typical of non-circular gear systems useful with the invention which system comprises 3 identical gears. A shaft 130 drives centrally-located gear 132. Gear 132, inturn, causes gears 134 and 136 to turn. The crank arms are affixed to the gears to operate at 180° out of phase with one another.

Figure 7:
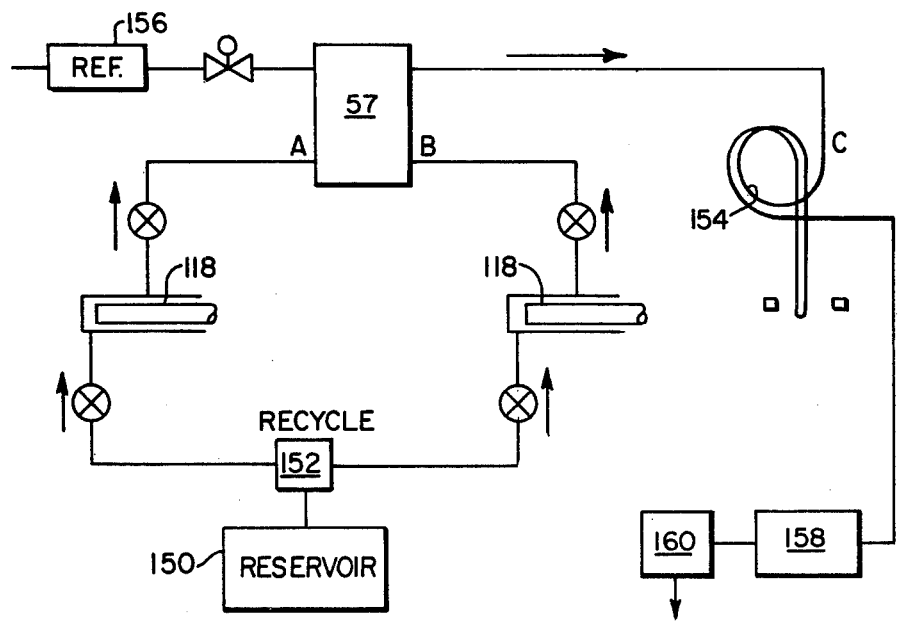
FIG. 7 is a schematic diagram of a chromatography system incorporating the invention.

FIG. 7 shows a complete liquid flow schematic of a liquid chromatography system of the type described herein. The liquid to be analyzed is maintained in a reservoir 150. Material to be analyzed is pushed into manifold 152 and into pump chambers 118 and a manifold 57. From manifold 57, the flow may be all caused to go through a pressure-sensor such as Bourdon tube 154 or, alternatively, it may be partly diverted to a reference means 156.

From the pressure sensor 154, the material to be analyzed is pumped through a chromatography column 158, thence to an analytical device 160.

The device described will allow fluid to be pumped at a substantially constant rate, i.e. at an output of plus or minus 1% from stroke to stroke; therefore flow will be essentially pulseless.

Figure 8:
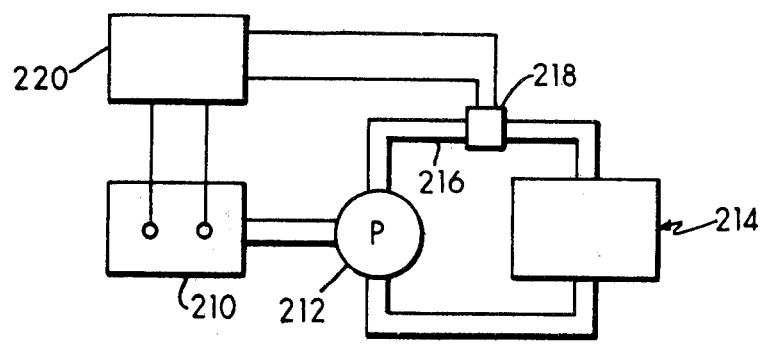
FIG. 8 is a highly schematized block and line diagram of motor control used in connection with the present invention.

In FIG. 8, a motor 210 drives a pump 212 which supplies fluid under pressure to a utilization device 214 by way of a fluid line 216 having a pressure transducer 218 in it. The transducer 218 supplies electrical signals indicative of the pressure in line 216 to a control unit 220 connected to motor 210. The unit 220 controls the driving current applied to the motor 210. The motor 210 is preferably a stepping motor, that is, it has a number of distinct driving coils which can be separately energized to drive a rotor through steps of discrete angular increment. It is desired that the driving current applied to this motor be only such as to drive the load to which the motor is connected and that excessive driving current, which results in increased heat dissipation, not be applied to the motor. The control unit 220 performs this function, among others.

Figure 9:
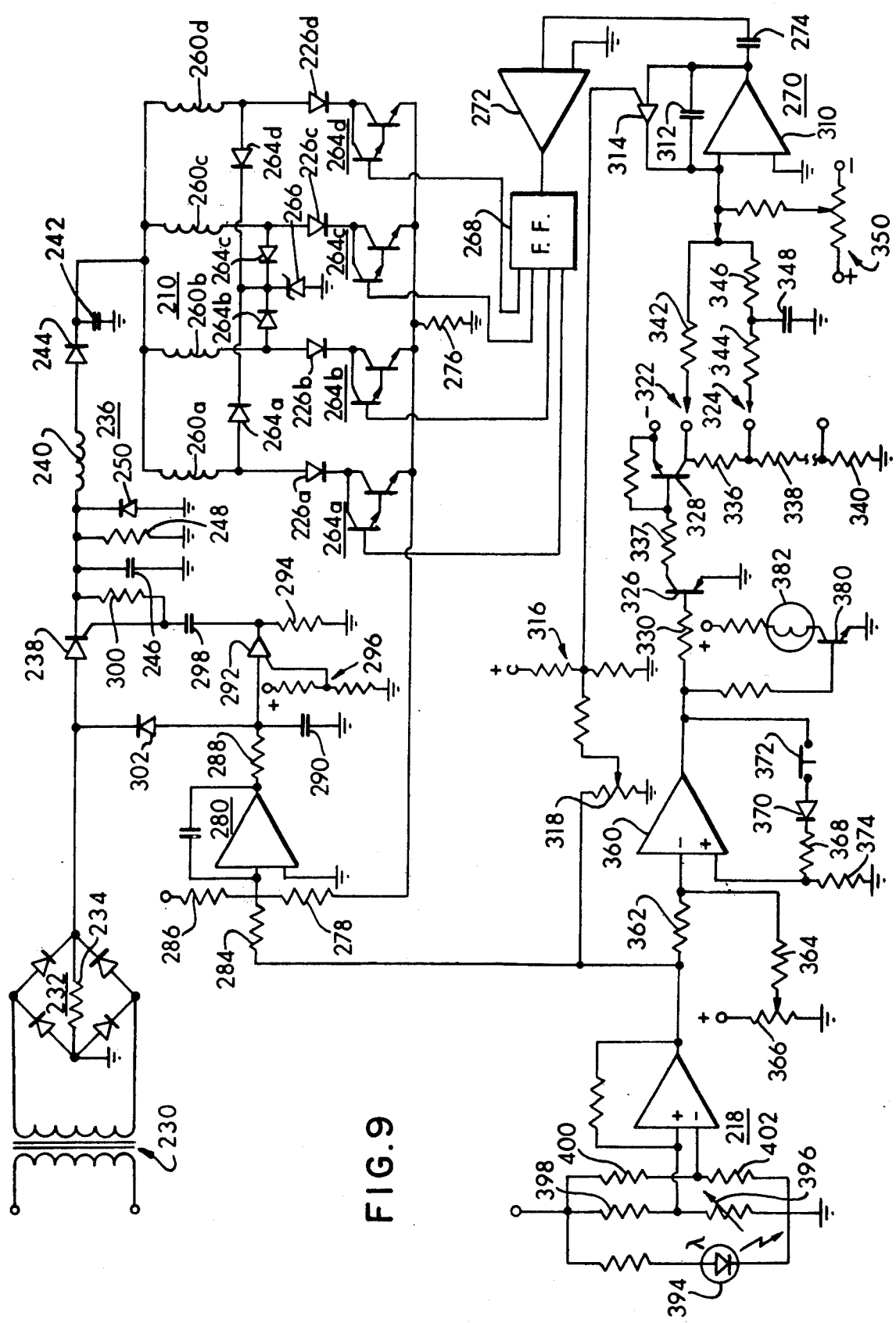
FIG. 9 is a schematic diagram of a preferred form of control circuit useful in the present invention.

Turning now to FIG. 9, the control circuit on the present invention is shown in detail. In FIG. 9, a transformer 230 has a primary winding connected to an AC power source and a secondary winding connected across a full-wave diode bridge rectifier 232. The bridge 232 has a resistor 234 connected from its output terminal to ground for reasons to be described hereinafter. The output of the bridge 232 is applied to a filter 236 through a controllable switching element preferably in the form of a silicon controlled rectifier 238. The filter 236 is formed from an inductor 240, capacitor 242, and diode 244. A capacitor 246, resistor 248, and diode 250 are interposed between the filter 236 and rectifier 238 for reasons described hereafter.

Figure 10:
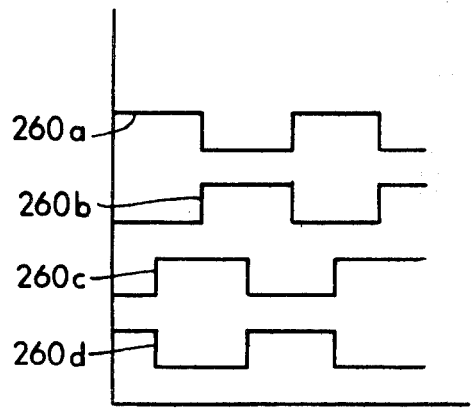
FIG. 10 is a sketch of driving wave forms for the circuit of FIG. 9.

The output of filter 236 is applied to control windings 260a–260d of motor 210. The motor 210 is a stepping motor having a permanent magnet rotor and pairs of bifilar-windings, that is coils 260a and 260b are bifilar wound as are coils 260c and 260d. Motors of this type are sold under the mark Slo-Syn by the Superior Electric Company. The motor windings are connected in series with diodes 262a–262d as well as with the collector-emitter of transistor pairs 264a–264d connected in a Darlington configuration. Diodes 264a–264d are connected from one of the inductors 260a–260d, respectively, to ground through a Zener diode 266. The conduction state of the transistor pairs 264a–264d is controlled by the outputs of a flip-flop 268. The flip-flop 268 is a 4-phase flip-flop commonly known as a "Johnson" flip-flop or a "Johnson" counter which provides output pulses on four discrete leads, each pulse having a duration of approximately 180°. The pulses are of positive polarity such that, when applied to the base of the respective transistor pairs 262a–262d, they cause these transistors to conduct so that current is drawn down through the corresponding motor winding to step the motor to a new angular position. The control outputs of flip-flop 268, and thus the driving currents in windings 260a–260d, are shown in FIG. 10. Flip-flop 268 is driven from an oscillator 270 through an amplifier 272 and a capacitor 274. Oscillator 270 will be described in detail hereafter.

The current being drawn through the motor 210 at any given time is sensed by means of a resistor 276 and a voltage proportional to this current is applied through a resistor 278 to the summing junction of an integrator 280. A second input is applied to the integrator from a pressure transducer 218 through a resistor 284. A negative bias current is also supplied to integrator 280 through a resistor 286. The common node to which resistors 278, 284 and 286 are connected comprises a summing junction and the output of integrator 280 is the time sum of the net current injected into this node. This output is applied through a resistor 288 to a capacitor 290. The charge on the capacitor 290 is discharged through a unijunction transistor 292 into a resistor 294. The firing point of the unijunction transistor 292 is determined by means of a voltage applied to its gate through a voltage divider network 296.

When sufficient charge has been accumulated on capacitor 290 to cause transistor 292 to conduct, a voltage is generated across resistor 294 which is coupled through a capacitor 298 to the gate of the silicon controlled rectifier 238 to turn the rectifier "on" and thus connect the output of bridge 232 to filter 236. A resistor 300 connected between gate and cathode of rectifier 238 helps to insure turn-off of the rectifier.

The integrator 280 compares the current called for by both the pressure sensor 218 and the fixed bias source connected to resistor 286 with the current actually supplied to the motor 210. As long as the motor current is less than that called for, the integrator 280 supplies an output which charges capacitor 290 with its upper electrode positive with respect to ground. The rate at which capacitor 290 is charged depends on the net current applied to the integrator input; the larger this current, the greater is the rate at which capacitor 290 is charged, the earlier the point at which the unijunction transistor 296 is triggered, and thus the earlier the rectifier 238 is fired. As the firing point of rectifier 238 advances in each half wave, it delivers more power to the filter 236 and thus to the motor 210.

In order to insure fine control of power supplied to the motor 210, the charge on capacitor 290 is dumped during each half cyclee of the full wave rectified output from the bridge rectifier 232. This is accomplished by means of a diode 300 which is connected to the bridge output. Each time the bridge output drops below the voltage on capacitor 290, the capacitor discharges to ground through diode 300 and resistor 234.

As the power demands of the load increase, the point at which the rectifier 238 fires shifts to a point earlier and earlier in each half-wave cycle. When the firing point lies between 90° and 180° in the half-wave cycle, the voltage at the filter output will generally be less than that applied to the anode of the controlled rectifier and the rectifier will fire normally to maintain the required filter output voltage. If more power is demanded, the firing point is advanced toward 90° and the anode voltage is made even larger than the output voltage at firing time. When, however, the firing point is advanced beyond 90° toward 0°, the anode voltage at firing time drops and may become less than the filter output voltage. Normally, this would cause the rectifier to misfire, the output voltage would drop, and the control would advance the firing point to an even earlier position so that the rectifier would quickly block. This is avoided in the present circuit by the provision of capacitor 246 and resistor 248. Capacitor 246 provides a low-impedance path to ground for initial rectifier turn-on, hold resistor 248 provides a DC current path through which a "trickle" current (current of small magnitude) can flow should the rectifier be fired prematurely (that is, when the filter output voltage is greater than the rectifier anode voltage). This current is maintained until the anode voltage rises above the output voltage during the 0–90° portion of the power cycle.

The inductor 236, in connection with capacitor 242, filters the wave-form passed by rectifier 238 and provides a nearly smooth DC voltage for motor 210. It does this by limiting the current surges associated with turn-on and turn-off storing energy during the transient changes and then delivering it over subsequent and longer time intervals to thereby smooth any peak surges and limit ohmic losses in the motor and elsewhere. When the current flow from rectifier 238 is cut off at the end of each half cycle, the inductor 240 generates a reverse voltage which tends to maintain current flow in the inductor for a brief interval. This current would naturally be drawn through rectifier 238 and thus this rectifier would tend to remain "on". To prevent this, a diode 250 is connected from ground to the inductor and provides a path through which the transient current for inductor 240 may be drawn, thus allowing rectifier 238 to turn off.

Limiting the current applied to the motor in the manner described limits the ohmic losses in the motor and its associated circuitry and thus significantly lowers the power dissipation and heat level of the motor and its controller. This prolongs motor life, lowers ambient temperature, and simplifies circuit design problems by minimizing the temperature range over which the control circuit is required to operate. Additionally, however, it extends the speed range over which the motor achieves a given torque level. The reason for this is that the motor is inductive at high speeds and must be fed from a higher potential source (e.g. 15 volts), but is resistive at low speeds being then fed from a lower potential source (e.g. 2 volts). A series resistor is usually inserted in the current supply leads to limit the current at low speeds; unfortunately, this also limits the current that can be drawn at high speeds and thus the output torque diminishes at high speeds. This is obviated by the control circuit of the present invention which sets the current drawn at all times to that required to drive the load.

As was previously noted, the windings 260a and 260b, as well as the windings 260c and 260d, are bifilar wound and thus magnetically coupled to each other. I have found that it is this coupling which in fact largely causes the oscillations or "resonance" effects noted in stepping motors of this type. Considering the current in each winding to be in the positive or forward direction when it flows downward in the windings in FIG. 9 and in the negative or reverse direction when it flows upward in these windings, the motor 210 is designed to operate properly when positive current flows in the windings in accordance with the schedule shown in FIG. 10. However, due to inductive coupling between the windings, a large negative voltage is coupled to winding 260b when current in winding 260a turns off, and vice versa. The same is true of windings 260c and 260d. This voltage greatly exceeds the forward driving voltage from the power supply and it forward-biases the base-collector path of the transistor switch with which it is associated. Thus, it causes a current in the reverse direction through the transistor and through the winding. It is this current which causes the undesired motor oscillations, since it momentarily drives the motor in the reverse direction. If the switch used to control the current in each winding were in fact a perfect switch having infinite impedence, no reverse current could flow, despite the reverse voltage and the motor would not oscillate. However, practical switches are always less than ideal and thus may conduct substantial reverse current.

Having thus recognized the problem, its harmful effects are mitigated simply by placing a diode in series with each motor winding and oriented such as to pass current through the winding when the associated transistor switch is turned "on" in response to a control input and to block current from passage through the winding when the transistor is "off". This is the function of diodes 262a–262d in series with the windings 260a–260d respectively. In the forward direction these diodes present a very low impedance to current flow; in the reverse direction, however, they present an extremely high impedance to current flow and thus effectively protect the motor against reverse current flow caused by voltages coupled in from other windings.

Returning now to oscillator 270, the oscillator 13 formed from an amplifier 310, a capacitor 312, and a unijunction transistor 314. The transistor 314 has a control potential applied to it from a voltage divider 316 as well as from a potentiometer 318 which is connected between the output of pressure transducers 218 and ground. The oscillator 270 receives an input from a switching network 320 through first and second independently actuable switches 322 and 324, respectively. The network 320 comprises transistors 326 and 328 and resistors 330, 322 and 334. A source of negative potential is applied to the emitter of transistor 328 and is coupled to a number of series-connected resistors 336, 338, 340, etc. in the collector circuit of transistor 328 when this transistor is turned "on". The resistor string 336–340 has intermediate terminals or "taps" at which selected fractions of the voltage applied at the emitter of 328 may be obtained. The voltages at the taps selected by switches 320 and 324 are coupled to the oscillator 270 through a resistor 342 in the case of switch 322 and through resistors 344 and 346 and capacitor 348 in the case of switch 324.

The magnitude of resistor 342 is such that as switch 322 moves from one tap to another on switching network 320, the current supplied through resistor 324 to oscillator 270 changes by one unit. Similarly, the magnitude of the resistors 344 and 346 is such that as switch 324 moves from tap to tap along the switching network 320, the magnitude of the current supplied through these resistors to oscillator 270 changes by 10 units. The capacitor 348 slows the rate at which the current to oscillator 270 is allowed to change when the switch 324 moves from tap to tap. A biasing current of selectable polarity is also applied to oscillator 270 from a network 350.

Oscillator 270 comprises a very simple yet effective sawtooth wave generator. The amplifier 310 and capacitor 312 form an integrator which provides an output voltage proportional to the magnitude and polarity of the current supplied to its input. The time constant of the integrator, which is determined by the capacitor 312 and by the magnitudes of the impedances connected to its input, is such that the output voltage rises essentially linearly during the time over which the integrator is to integrate. When the output voltage reaches a magnitude equal to that applied to the gate of unijunction transistor 314, this transistor "fires", thus discharging the capacitor 312 through it. After firing, the transistor 314 turns "off" and capacitor 312 again starts charging. Thus a repetitive ramp wave form is generated. The duration of the ramp is determined by the magnitude of the signal applied to the input of oscillator 270, as well as by the magnitude of the gate control signal on transistor 314. By decreasing the latter, or increasing the former, the repetition frequency of the oscillator for 270 is increased. Conversely, it is decreased by increasing the magnitude of the gating signal applied to the transistor 314 or by decreasing the driving input applied through the switches 342 and 344.

The operation of switching network 320 is controlled from an amplifier 360 which has an input connected through a resistor 362 to the output of pressure sensor 218 and through a resistor 364 to the wiper arm on a potentiometer 366 to which a positive biasing potential is applied. A resistor 368, a diode 370 and a pushbutton switch 372 are connected between one input of the amplifier 360 and its output, and a resistor 374 is connected between this input and ground.

The amplifier 360 compares the output of pressure sensor 218, which is proportional to the pressure in the fluid line driven by motor 210, with a preestablished "set point" determined by the setting of potentiometer 366. As long as the pressure corresponding to the output of the sensor 218 is less than that corresponding to the set point, the output of amplifier 360 is negative. This holds the transistors 326 and 328 "on", and a portion of the negative potential applied to the emitter of transistor 328 is therefore coupled through the thumb wheel switches 322 and 324 to oscillator 270. When, however, the pressure rises to such a point that the output of pressure sensor 218 exceeds that corresponding to the set point of potentiometer 366, the output of amplifier 360 switches to a positive polarity, transistors 322 and 324 are turned "off", and the input to oscillator 270 from switches 322 and 324 is cut off. The oscillator is thus effectively disabled, except for a residual driving current supplied to it from potentiometer 350.

When the output of pressure sensor 218 exceeds that obtained from potentiometer 366, the output of amplifier 360 goes positive, diode 370 conducts and feeds a portion of the output back to the input. This rapidly drives the amplifier to saturation and holds it in the saturated state such that it is thereafter insensitive to any changes in the input. The positive output of amplifier 360 turns off transistor 326 and thus transistor 328. Further, it turns on a transistor 380 and lights a warning light 382 to indicate that preset pressure limits have been exceeded. The amplifier 360 is reset by means of pushbutton switch 372. Momentarily depressing this switch disconnects the positive feedback around the amplifier and allows it to return to its usual monitoring state.

As noted earlier, the period of oscillator 270 can be changed by changing its input or by changing the control voltage applied to the gate of unijunction transistor 314. As the pressure in the line to which motor 210 is connected increases, the output of pressure sensor 218 becomes increasingly negative. This output is coupled through potentiometer 318 to the gate of transistor 314 and thus the control potential on this gate is lowered as the pressure increases. This increases the repetition frequency of the oscillator 270 and thus speeds up the motor 210. Accordingly, as the compression in the line increases due to pressure of the fluid increasing in the line, the motor driving rate is speeded up in order to maintain a constant mass flow rate. This is desirable in applications such as chromatography.

Figure 11:
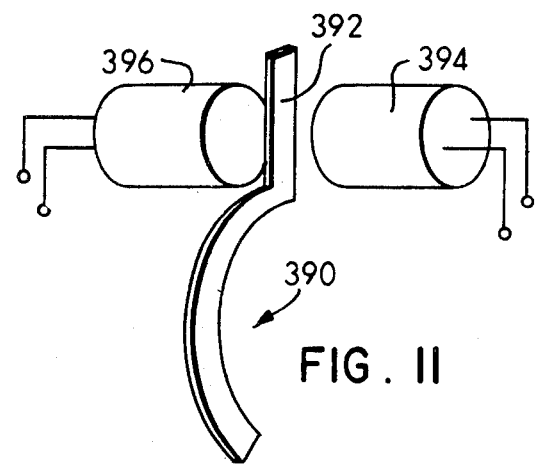
FIG. 11 is a sketch of a pressure gage useful in the present invention.

The pressure sensor 218 of the present invention is especially simple in design and operation. Referring briefly to FIG. 11, the sensor is formed from a mechanical pressure sensor such as Bourdon tube 390 having a mechanically movable indicator element 392 which moves between a light source 394 and a light responsive transducer such as a photocell 396. The tube 390 is connected into the fluid line whose pressure is being measured, as the tube moves the indicator 392 to block a greater or lesser amount of light from the photocell 396 and the resistance of this cell thus varies in accordance with line pressure.

Referring back to FIG. 9, the photocell 396 is connected in a bridge circuit with resistors 396, 398, 400 and 402. The bridge output, which is proportional to the resistance of photocell 396 and thus to the position of indicator 392 in response to the fluid line pressure, is applied to an amplifier 404 which provides an output proportional to the deviation of this pressure from a convenient "zero point" determined by the magnitude of resistors 398–402. For the configuration shown, this output preferably ranges between 0 volts and some negative voltage level. This voltage determines the motor driving rate and motor drive current as previously described.

Figure 12:
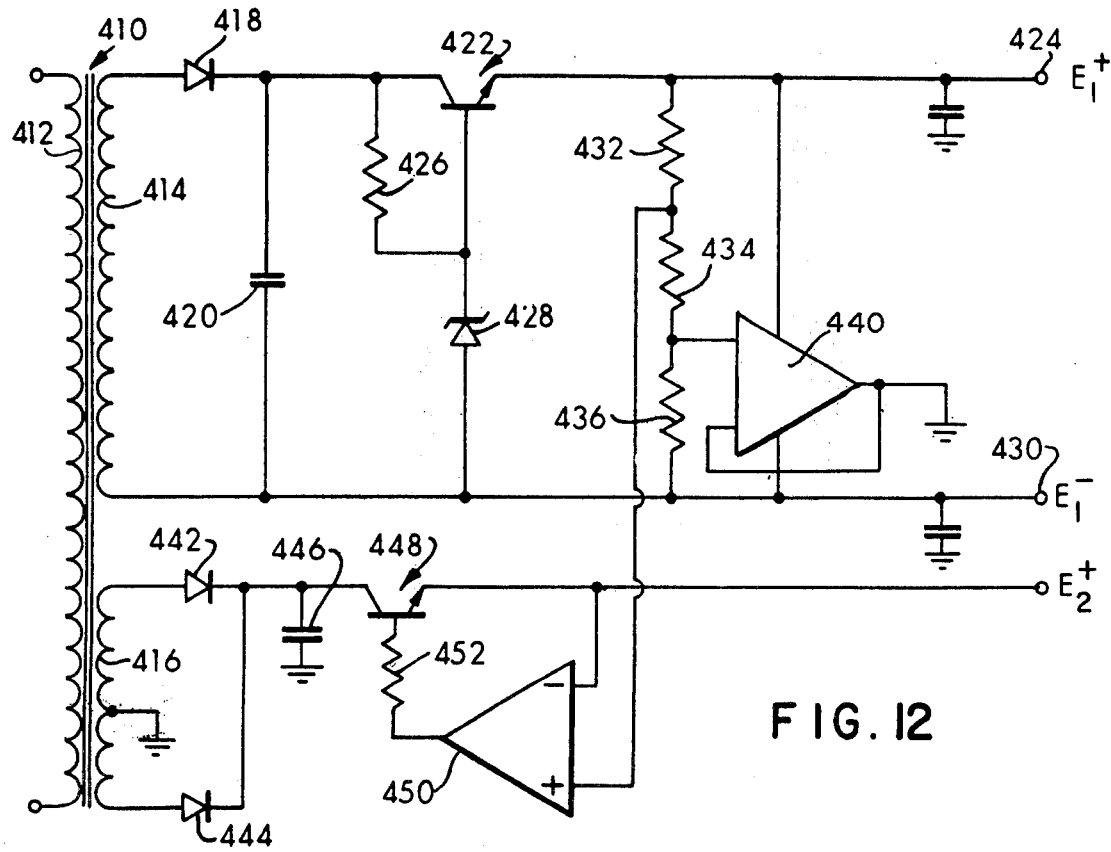
FIG. 12 is a schematic diagram of a power supply useful in the present invention.

Turning now to FIG. 12, an especially advantageous power supply for supplying the necessary voltages for the active elements in the control circuit is shown. In FIG. 12, a transformer 410 has a primary winding 412 and a pair of secondary windings 414 and 416. The winding 414 has a diode 418 in series with it and a capacitor 420 connected across it. A series pass regulator in the form of a transistor 422 controls the voltage drop between the cathode of diode 418 and a first output terminal 424. A resistor 426 is connected from collector to base of transistor 422 and a zener diode 428 is connected between base and a second output terminal 430. Voltage divider resistors 432, 434 and 436 are connected across terminals 424 and 430.

An amplifier 440 has one input terminal connected between the junction of resistor 434 and 436 and a second input terminal connected to its output terminal and thence to ground. The amplifier 440 is chosen to have sufficiently high gain (of the order of tens of thousands or more) such that the junction of resistors 434 and 436 is effectively at ground potential. In this case, terminal 424 is thus at a potential above ground, while terminal 430 is at a potential below ground. The power inputs for amplifier 226 are taken from the terminals 424 and 426.

The amplifier 440 effectively provides a low impedence return path to ground for currents drawn from terminals 424 or 430. If the junction of resistors 434 and 436 were directly grounded without the use of such an amplifier, the return path to ground would include the resistors 432 and 434 in case of current drawn from terminal 424, and would include resistor 436 in the case of current drawn from terminal 430. The currents through these resistors would vary with the load demands and this the output voltage would vary accordingly. Through the use of amplifier 440, however, this effect is mitigated and the voltage regulation of the power supply is this greatly improved.

An auxiliary power supply is formed from transformer secondary winding 416, which is center-tapped, in connection with diodes 442 and 444 which provide full wave rectifivation for the voltage applied across transformer 416. A filter and regulator if formed from capacitor 446, series pass regulator transistor 448, and amplifier 450 and resistor 452. The auxilliary supply receives a reference voltage from the common connection point of resistors 432 and 434 in the primary power supply. The auxilliary power supply is otherwise conventional and will not be described in further detail.

From the foregoing, it will be seen that there is provided an improved motor control circuit. The circuit limits power dissipation in a stepping motor by limiting the motor drive current to that demanded by the load, so that heat dissipation in the motor is kept to a minimum. In connection with the control circuit, there is provided a useful driving circuit for operating a silicon-controlled rectifier in a phase-controlled power supply network and additionally have provided a very simple yet effective variable frequency oscillator for use in conjunction with a motor drive circuit.

Further, there is provided an inexpensive and useful power supply for supplying the active elements in a control circuit.

Moreover, undesired oscillations or resonances formerly encountered in connection with driving a stepping motor have been inexpensively, yet effectively, obviated.

What is claimed is:

1. A positive-displacement pump comprising a plurality of pump chambers,
   plungers positioned for reciprocal motion in each said chamber, and operating means for moving said plungers independently from one another;
   said operating means including means to synchronize the movement of plungers in said chambers to maintain the sum of fluid flowing from all said chambers at a substantially constant displacement rate,
   said pump adapted to hold less than about 3 milliliters liquid volume,
   means for pushing each said plunger assembly foward to an extended position within its chamber wherein it largely fills said chamber,
   means for pulling each said plunger backwards to a retracted position wherein it is largely removed from its chamber,
   seal means between each said chamber and said push and pull means; and wherein
   a fluid inlet is positioned at an inlet end of each said chamber,
   a fluid outlet is positioned at an outlet end of each said chamber,
   wherein each said plunger, in extended position, forms a thin annular conduit with the chamber wall, said conduit forming means for fluid first entering said chamber at one said port during said plunger's movement from the extended position to the retracted position, to be also the fluid first discharged from said chamber at the second said port as the plunger returns to its extended position;
   wherein said pump is free of additional structure between said fluid inlet and said fluid outlet;
   and wherein said system comprises a flow path comprising said outlet from said system for supplying a liquid under pressure, and interposed between said pump and said system outlet, a liquid-pressure sensing means and, operably communicating between said pressure-sensing means and a motor drive means for said pump, a motor control means operably interacting with said motor drive means to continuously control the flow-output of said pump by continuously controlling the speed of said motor in response to said pressure.

2. Apparatus as defined in claim 1 wherein said annular conduit is from 0.001 to 0.005 inches in width.

3. A liquid delivery system as defined in claim 1 wherein no part of the flow path is more than about 0.2 inches from the main center line of the flow path of the liquid.

4. A liquid delivery system of claim 1 wherein substantially all liquid-receptive volume between the inlet of said pump chamber and said discharge port from said chamber is flushed by each cycle of said liquid pump.

5. A positive-displacement type pump having a) a plurality of pistons, each operating in a different chamber; b) piston-driving means; and c) piston-synchronizing means; said pistons, driving means, and synchronizing means together forming means to discharge a substantially constant flow of liquid from said pump to said discharge port and wherein substantially all liquid-receptive volume between the inlet of each said pump chamber and the discharge port therefrom is flushed on each cycle of the piston operating in said chamber, and wherein said flow is within plus or minus 1% and wherein the internal volume of liquid within said pump is less than about 3 milliliters.

6. A pump as defined in claim 5 wherein all loci within a volume of liquid within said pump are less than about 0.2 inches from the mean flow path through said pump.

7. In a liquid delivery system of the type comprising a pump and outlet useful for supplying, a liquid under pressure, from said outlet, the improvement wherein there is interposed between said pump and a discharge port from said delivery means 1) a pressure-sensing means and 2) motor-control means operably communicating between said pressure-sensing means and a motor drive means for said pump, said control means operably interacting with said drive means to control the flow-output of said pump by controlling the speed of said motor, and wherein substantially all liquid-receptive volume between the inlet of said pump chamber and the outlet port of said system is flushed by each cycle of said liquid pump; and
   wherein no part of the flow path is more than about 0.2 inches from the mean center line of the flow path of the liquid through said pump.

8. A liquid delivery system as defined in claim 7 wherein the flow discharge from said pump is within plus or minus 1%.

9. A positive-displacement pump comprising a plurality of pump chambers, plungers positioned for reciprocal motion in each said chamber, and operating means for moving said plungers independently from one another;

said operating means including means to synchronize the movement of plungers in said chambers to maintain the sum of fluid flowing from all said chambers at a substantially constant displacement rate, said pump adapted to hold less than about 3 milliliters liquid volume, means for pushing each said plunger assembly forward to an extended position within its chamber wherein it largely fills said chamber, means for pulling each said plunger backwards to a retracted position wherein it is largely removed from its chamber, seal means between each said chamber and said push and pull means; and wherein a fluid inlet is positioned at an inlet end of each said chamber, a fluid outlet is positioned at an outlet end of each said chamber, and wherein each said plunger, in extended position, forms a thin annular conduit with the chamber wall, said conduit forming means for fluid first entering said chamber at one said port during said plunger's movement from the extended position to the retracted position, to be also the fluid first discharged from said chamber at the second port as the plunger returns to its extended position;

and wherein said pump is free of additional structure between said fluid inlet and said fluid outlet;

A. said plunger assembly is free of positive mechanical connection to said pushing means, B. said pulling means is a biasing means adapted to be compressed by said pushing means during the forward stroke thereof, then to expand during a retraction of said pushing means, keeping the plunger biased against said pushing means during the backward stroke thereof.

10. Apparatus as defined in claim 9 wherein substantially all of the fluid-filled space within said pump is flushed on each forward stroke of said plunger assembly.

11. Apparatus as defined in claim 9 wherein the contact between said plunger and said pushing means is a point contact between said plunger assembly and a spherical surface on said plunger means.

12. Apparatus as defined in claim 9 wherein said seal means is formed of a self-lubricating polymeric material.

13. Apparatus as defined in claim 12 wherein the contact between said plunger assembly and said pushing means is via a cylindrical surface on said plunger means.

14. In a positive-displacement pump comprising (1) a plunger assembly positioned for reciprocal motion in a pump chamber having an inlet port to said pump and an outlet port from said pump, thereby forming means to alternately pull fluid into the chamber and push fluid out of the chamber and out of the pump, (2) means for pushing said plunger assembly forward to an extended position wherein it largely fills said chamber, (3) means for pulling said plunger backwards to a retracted position wherein it is largely removed from said chamber, and (4) seal means between said chamber and said push and pull means the improvement wherein a fluid inlet is positioned at an inlet end of said chamber;

a fluid outlet is positioned at an outlet end of said chamber;

wherein said plunger, in extended position, forms an annular conduit with the chamber wall, said conduit forming means for fluid first entering said chamber at one said port, during said plunger's movement from the extended position to the retracted position, to be also the fluid first discharged from said chamber at the second said port as the plunger returns to its extended position;

and wherein said pump has a) a plurality of pistons, each operating in a different chamber; b) piston-driving means; and c) piston-synchronizing means; said pistons driving means, and synchronizing means together forming means to discharge a substantially constant flow of liquid from said pump to said discharge port and wherein substantially all liquid-receptive volume between the inlet of each said pump chamber and the discharge port therefrom is flushed on each cycle of the piston operating in said chamber.

15. A liquid delivery system as defined in claim 1 wherein each incremental volume of liquid in the liquid flow path between the pump and the outlet of said system is substantially flushed on each cycle of each piston.

* * * * *

UNITED STATES PATENT OFFICE
CERTIFICATE OF CORRECTION

Patent No. 3,981,620        Dated September 21, 1976

Inventor(s) Louis Abrahams, Burleigh M. Hutchins, Jr. & James L. Waters

It is certified that error appears in the above-identified patent and that said Letters Patent are hereby corrected as shown below:

Column 10, line 32:    change "13" to --is--

Column 10, line 39:    delete "320"

Column 10, line 41:    delete "320"

Column 10, line 56:    delete "320"

Column 10, line 60:    delete "320"

Column 10, line 42:    change "322" to --337--

Column 10, line 50:    change "320" to -322--

Column 13, line 14:    change "rectifivation" to --rectification--

Column 13, line 15:    change "if" to --is--

Signed and Sealed this

Tenth Day of May 1977

[SEAL]

Attest:

RUTH C. MASON
*Attesting Officer*

C. MARSHALL DANN
*Commissioner of Patents and Trademarks*